(12) United States Patent
Edelmann et al.

(10) Patent No.: US 6,444,873 B1
(45) Date of Patent: Sep. 3, 2002

(54) MSH5 ABLATED MICE AND USES THEREFOR

(75) Inventors: Winfried Edelmann, Bronx, NY (US); Richard D. Kolodner, San Diego, CA (US); Jeffrey W. Pollard, New York, NY (US); Raju S. Kucherlapati, Darrien, CT (US)

(73) Assignees: Albert Einstein College of Medicine of Yeshiva University, Bronx, NY (US); Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 09/469,636

(22) Filed: Dec. 22, 1999

Related U.S. Application Data

(60) Provisional application No. 60/113,487, filed on Dec. 22, 1998.

(51) Int. Cl.$^7$ ............ A01K 67/00; A01K 67/033; G01N 33/00; C12N 15/00
(52) U.S. Cl. ............ 800/18; 800/3; 800/25
(58) Field of Search ............ 800/8, 3, 9, 18, 800/25

(56) References Cited

FOREIGN PATENT DOCUMENTS

WO    WO 9901550    1/1999

OTHER PUBLICATIONS

Moreadith et al, 1997, J. Mol. Med., 75: 208–216.*
Mullins et al, 1996, J. Clin. Invest., 98(11): S37–S40.*
Seamark et al, 1994, Reprod. Fert. Dev., 6: 653–657.*
Akiyama Y, et al. "Germ–line mutation of the hMSH6/GTBP gene in an atypical hereditary nonpolyposis colorectal cancer kindred". *Cancer Res.* 1997 Sep. 15;57(18):3920–3.
Bawa S, et al., A mutation in the MSH5 gene results in alkylation tolerance. *Cancer Res.* Jul. 1, 1997; 57(13):2751–20
Baker SM, et al. "Involvement of mouse Mlh1 in DNA mismatch repair and meiotic crossing over." *Nat Genet.* Jul. 1996;13(3):336–42.
Baker SM, et al. "Male mice defective in the DNA mismatch repair gene PMS2 exhibit abnormal chromosome synapsis in meiosis." *Cell.* Jul 28, 1995; 82(2):309–19.
de Vries SS, et al. "Mouse MutS–like protein Msh5 is required for proper chromosome synapsis in male and female meiosis". *Genes Dev.* Mar. 1, 1999;13(5):523–31.
Edelmann W, et al. "Meiotic pachytene arrest in MLH1–deficient mice". *Cell.* Jun. 28, 1996;85(7):1125–34.
Hollingsworth NM, et al., "MSH5, a novel MutS homolog, facilitates meiotic reciprocal recombination between homologs in Saccharomyces cerevisiae but not mismatch repair." *Genes Dev.* Jul. 15, 1995; 9(14):1728–39.

Kolodner R. "Biochemistry and genetics of eukaryotic mismatch repair". *Genes Dev.* Jun. 15, 1996;10(12):1433–42.

Leach FS, et al. "Mutations of a mutS homolog in hereditary nonpolyposis colorectal cancer".*Cell.* Dec. 17, 1993;75(6):1215–25.

Miyaki M, et al. "Germline mutation of MSH6 as the cause of hereditary nonpolyposis colorectal cancer."*Nat Genet.* Nov. 1997;17(3):271–2.

Modrich P, et al. "Mismatch repair in replication fidelity, genetic recombination, and cancer biology". *Annu Rev Biochem.* 1996;65:101–33.

Moreadith RW, et al. "Gene targeting in embryonic stem cells: the new physiology and metabolism".*J Mol Med.* Mar. 1997; 75(3):208–16.

Mullins, L, J et al. "Transgenesis in the Rat and Larger Mammals" *J. Clin. Invest.* 1996; 98: s37–s40.

Papadopoulos N, et al. "Mutation of a mutL homolog in hereditary colon cancer." *Science.* Mar. 18, 1994;263(5153):1625–9.

Pochart P, et al. "Conserved properties between functionally distinct MutS homologs in yeast." J Biol Chem. Nov. 28, 1997;272(48):30345–9.

Reitmair AH, et al. "MSH2 deficient mice are viable and susceptible to lymphoid tumours." *Nat Genet.* Sep. 1995;11(1):64–70.

Ross–Macdonald P, et al. "Mutation of a meiosis–specific MutS homolog decreases crossing over but not mismatch correction." *Cell.* Dec. 16, 1994;79(6):1069–80.

Seamark RF. "Progress and emerging problems in livestock transgenesis: a summary perspective". *Reprod Fertil Dev.* 1994;6(5):653–7.

Winand NJ, et al. "Cloning and characterization of the human and Caenorhabditis elegans homologs of the *Saccharomyces cerevisiae* MSH5 gene", *Genomics.* Oct. 1, 1998;53(1):69–80.

de Wind N, et al. "Inactivation of the mouse Msh2 gene results in mismatch repair deficiency, methylation tolerance, hyperrecombination, and predisposition to cancer". *Cell.* Jul. 28, 1995;82(2):321–30.

\* cited by examiner

*Primary Examiner*—Deborah Crouch
*Assistant Examiner*—Peter Paras, Jr.
(74) *Attorney, Agent, or Firm*—Lahive & Cockfield, LLP; Amy E. Mandragouras; Maria C. Laccotripe

(57) ABSTRACT

An animal, e.g., transgenic mouse, in which the MSH5 gene is misexpressed. The animal is useful for screening treatments for a number of conditions. Methods for identifying contraceptive agents are also described.

16 Claims, 10 Drawing Sheets

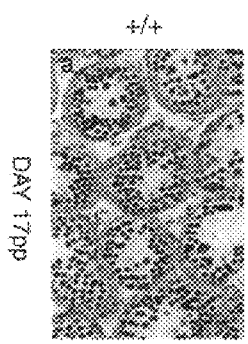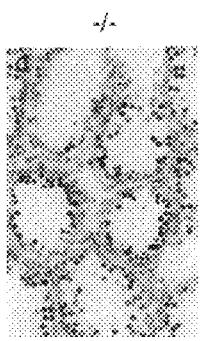
Fig. 3A  Fig. 3B  Fig. 3C  Fig. 3D
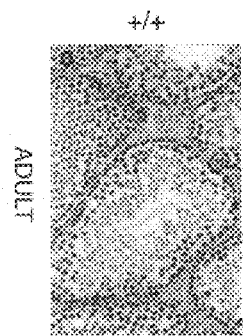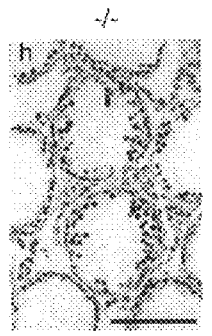
Fig. 3E  Fig. 3F  Fig. 3G  Fig. 3H

MSH5 ABLATED MICE AND USES THEREFOR

RELATED APPLICATIONS

This application claims priority to U.S. provisional application Ser. No. 60/113,487, filed on Dec. 22, 1998, incorporated herein in its entirety by this reference.

GOVERNMENT FUNDING

Work described herein was supported by funding from the National Institute of Health. The United States Government has certain rights in the invention.

FIELD OF THE INVENTION

The invention relates to animals in which the MutS homolog 5 (MSH5) gene is misexpressed and methods of using such animals or cells derived therefrom, e.g., in methods of evaluating fertility treatments.

BACKGROUND OF THE INVENTION

MutS homolog 5 (MSH5) is a member of a family of proteins that are known to be involved in DNA mismatch repair (Modrich, P. & Lahue (1996) *Annu. Rev. Biochem.* 65, 101–133; Kolodner, R. (1996) *Genes Dev.* 10, 1433–1442). Germ line mutations in MSH2, MLH1 and MSH6 cause hereditary non-polyposis colon cancer (HNPCC) or Lynch syndrome (Leach, F. S. et al. (1993) *Cell* 75, 1215–1225; Bronner, C. E. et al. (1994) *Nature* 368, 258–261; Papadopoulos, N. et al. (1994) *Science* 263, 1625–1629; Akiyama, Y. et al. (1997) *Cancer Res.* 57, 3920–3923; Miyaki, M. et al. (1997) *Nature Genet.* 17, 271–272). Inactivation of Msh2, Mlh1, Msh6 and Pms2 in mice leads to hereditary predisposition to intestinal and other cancers (de Wind, N.et al. (1995) *Cell* 82, 321–330; Reitmair, A. H. et al. (1995) *Nature Genet.* 11, 64–70). Early studies in yeast revealed a role for some of these proteins, including MSH5, in meiosis (Hollingsworth, N. M., et al. (1995) *Genes & Development* 9, 1728–1739; Ross-Macdonald, P. & Roeder, G. S. (1994) *Cell* 79, 1069–1080). Gene targeting studies in mice confirmed roles for MLH1 and PMS2 in mammalian meiosis (Baker, S. M. et al. (1995) *Cell* 82, 309–320; Edelmann, W. et al. (1996) *Cell* 85, 1125–1134; Baker, S. M. et al. *Nature Genet.* 13, 336–342).

SUMMARY OF THE INVENTION

The present invention is based, at least in part, on the generation of animals which are homozygous for a null mutation in the MutS homolog 5 (MSH5) gene and the observation that these animals are sterile. Accordingly, the invention features, a non-human animal, in which the gene encoding the MutS homolog 5 (MSH5) protein is misexpressed.

In preferred embodiments the animal, which is preferably a transgenic animal, is a mammal, e.g., a non human primate or a swine, e.g., a miniature swine, a monkey, a goat, or a rodent, e.g., a rat, but preferably a mouse.

In preferred embodiments, expression of the gene encoding the MSH5 protein is decreased as compared to the wild-type animal. For example, the levels of the MSH5 protein can be suppressed by, at least, 50%, 60%, 70%, 80%, 90%, or 100% as compared to the wild-type animal.

In preferred embodiments, misexpression of the gene encoding the MSH5 protein is caused by disruption of the MSH5 gene. For example, the MSH5 gene can be disrupted through removal of DNA encoding all or part of the protein.

In preferred embodiments, the animal can be heterozygous or homozygous for a misexpressed MSH5 gene, e.g., it can be a transgenic animal heterozygous or homozygous for an MSH5 transgene.

In preferred embodiments, the animal is a transgenic mouse with a transgenic disruption of the MSH5 gene, preferably an insertion or deletion, which inactivates the gene product.

In another aspect, the invention features, a nucleic acid molecule which, when introduced into an animal or cell, results in the misexpression of the MSH5 gene in the animal or cell. In preferred embodiments, the nucleic acid molecule, includes an MSH5 nucleotide sequence which includes a disruption, e.g., an insertion or deletion and preferably the insertion of a marker sequence. For example, a nucleic acid molecule can be the targeting construct shown in FIG. 1.

In another aspect, the invention features, a method of evaluating a fertility treatment. The method includes: administering the treatment to an MSH5 misexpressing animal, e.g., a transgenic mouse, or a cell therefrom; and determining the effect of the treatment on a fertility indication, e.g., sperm count, testicular size, or oocyte morphology, to thereby evaluate the treatment for fertility. The method may be performed in vivo or in vitro.

In preferred embodiments, the animal or cell is an animal or cell described herein. In other preferred embodiments, the method uses a transgenic mouse in which the expression of the MSH5 gene is inhibited. In yet other preferred embodiments, the method uses a cell derived from a transgenic mouse in which the expression of the MSH5 gene is inhibited.

In another aspect, the invention features, a method for identifying a compound which modulates the activity of MSH5. The method includes contacting MSH5 with a test compound and determining the effect of the test compound on the activity of MSH5 to, thereby, identify a compound which modulates MSH5 activity. In preferred embodiments, the activity of MSH5 is inhibited.

In another aspect, the invention features, a method for modulating the activity of MSH5. The method includes contacting MSH5 or a cell expressing MSH5 with a compound which binds to MSH5 in an amount sufficient (e.g., a sufficient concentration) to modulate the activity of MSH5. In preferred embodiments, the activity of MSH5 is inhibited, e.g., the method can be used in contraception.

In another aspect, the invention features, a method of identifying a subject having or at risk of developing a fertility disease or disorder. The method includes obtaining a sample from said subject; contacting the sample with a nucleic acid probe or primer which selectively hybridizes to MSH5 and determining whether aberrant MSH5 expression or activity exists in the sample, thereby, identifying a subject having or at risk of developing a fertility disease or disorder.

In another aspect, the invention features, an isolated cell, or a purified preparation of cells, from an MSH5 misexpressing animal, e.g., an MSH5 misexpressing animal described herein. In preferred embodiments, the cell is a transgenic cell, in which the gene encoding the MSH5 protein is misexpressed. The cell, preferably a transgenic cell can be an oocyte or a spermatocyte.

In preferred embodiments, the cell is heterozygous or homozygous for the transgenic mutant gene.

Other features and advantages of the invention will be apparent from the following detailed description, and from the claims.

BRIEF DESCRIPTION OF THE DRAWINGS

FIG. 1A depicts the gene targeting strategy. FIG. 1B is a depiction of a Southern blot of tail DNA digested with NsiI. DNA analysis of 606 offspring from heterozygote matings produced 184 Msh5$^{+/+}$, 275 Msh5$^{+/-}$ and 147 Msh5$^{-/-}$, confirming the Mendelian transmission of the mutant allele. FIG. 1C is a depiction of a Northern blot of RNA from Msh5$^{+/+}$ and Msh5$^{-/-}$ mouse testes with different probes. FIG. 1D is a depiction of a Western blot of proteins from male testes with anti-MSH5 antibody.

FIG. 2A is a depiction of the MRNA expression of Msh5 (upper panel) and actin (lower panel) in testes from wild-type males between the ages of 8 days and 29 days, and in adult wild-type and Msh5$^{-/-}$ males. FIGS. 2B–E are a depiction of H&E stained sections of adult testis from wild-type (B, D) and Msh5$^{-/-}$ (C, E) males showing loss of spermatocytes beyond zygonema in Msh5-deficient males. Le, Leydig cell; S, Sertoli cell; A, type A spermatogonia; B, type B spermatogonia; PL, pre-Leptotene; L, Leptotene spermatocyte; Z, Zygotene spermatocyte; P, Pachytene spermatocyte; RS, round spermatid; ES, elongated spermatid; Sp, spermatozoa. FIGS. 2F, G are a depiction of the immunolocalization of germ cells using anti-GCNA1 antibody (red immunoreactive protein against a light blue counterstain) on sections from wild-type (F) and Msh5$^{-/-}$ (G) testes from 29 day old males showing abundant spermatocytes, spermatids and spermatozoa in wild-type testes and a few GCNA 1-positive cells in the MSH5-deficient testes. (For B and C, scale bar=100 μm; for D–G, scale bar=25 μm).

FIGS. 3A–H depicts the progressive depletion of germ cells in Msh5$^{-/-}$ males during development. FIGS. 3A, B, E, F are a depiction of germ cell immunolocalization using the anti-GCNA1 antibody of testes from wild-type (A, E) and Msh5$^{-/-}$ (B, F) males showing the rapid depletion of germ cells from day 17 pp onwards in Msh5-deficient mice in contrast to the increasing density and variety of spermatogenic cells in the seminiferous tubules of Msh5$^{+/+}$ males. FIGS. 3C, D, G, H are a depiction of TUNEL staining of testes from wild-type (C, G) and Msh5$^{-/-}$ males (D, H) showing continuous apoptosis from day 17 pp onwards compared to the very low level of apoptosis in tubules from wild-type males over the same time frame. (Scale bar=100 μm.)

FIGS. 4A–C are a depiction of silver-stained spermatocytes from wild-type (A) and Msh5$^{-/-}$ (B, C) testes showing complete failure of pairing (B) or some partial pairing (C) in the absence of MSH5. Arrowheads in panel (C) indicate chromosomes exhibiting partial pairing. Note that many of these chromosomes appear to be unequally paired.

FIGS. 5A,B depicts ovaries from day 3 pp wild-type (A) and Msh5$^{-/-}$ (B) females showing oocytes stained with GCNA1. FIG. 5C depicts the entire ovary from a day 25 pp Msh5$^{-/-}$ female (H&E staining) containing only 3 follicles and degenerating tissue. FIG. 5D,E is a depiction of H&E stained ovaries from adult wild-type (D) and Msh5$^{-/-}$ females (E) showing complete loss of oocytes and ovarian architecture in the absence of Msh5. B, ovarian bursa; Ov, oviduct. In all cases, scale bar=200 μm. FIG. 5F is a depiction of the expression of ZP3 and Actin in ovaries of wild-type and Msh5$^{-/-}$ ovaries on day 25 pp and in the adult.

FIGS. 6A–D depicts ovaries from e18 wild-type (A,B) and Msh5$^{-/-}$ (C,D) embryos showing oogonia stained with anti-GCNA1 (A,C) or H&E localization of meiotic chromosome detail (C,D). FIGS. 6E–H depicts GCNA1 localization of oocytes in ovaries from day 3 pp wild-type (E,F) and Msh5$^{-/-}$ (G,H) females. Arrowheads indicate pachytene oocytes (punctate red staining of nucleus compared to solid red staining of pre-pachytene oocytes), arrows indicate the appearance of the earliest primordial follicles. FIGS. 6I, and 6J, are a depiction of GCNA1 localization of oocytes in ovaries from day 6 pp wild-type (I,J) females (overstained to stain oocytes in meiotic arrest). Arrows indicate primordial follicles; o, oocyte. For A, C, E, G, and I scale bar=100 μm; for B, D, F, H and j scale bar=25 μm.

DETAILED DESCRIPTION

Figure 1A:
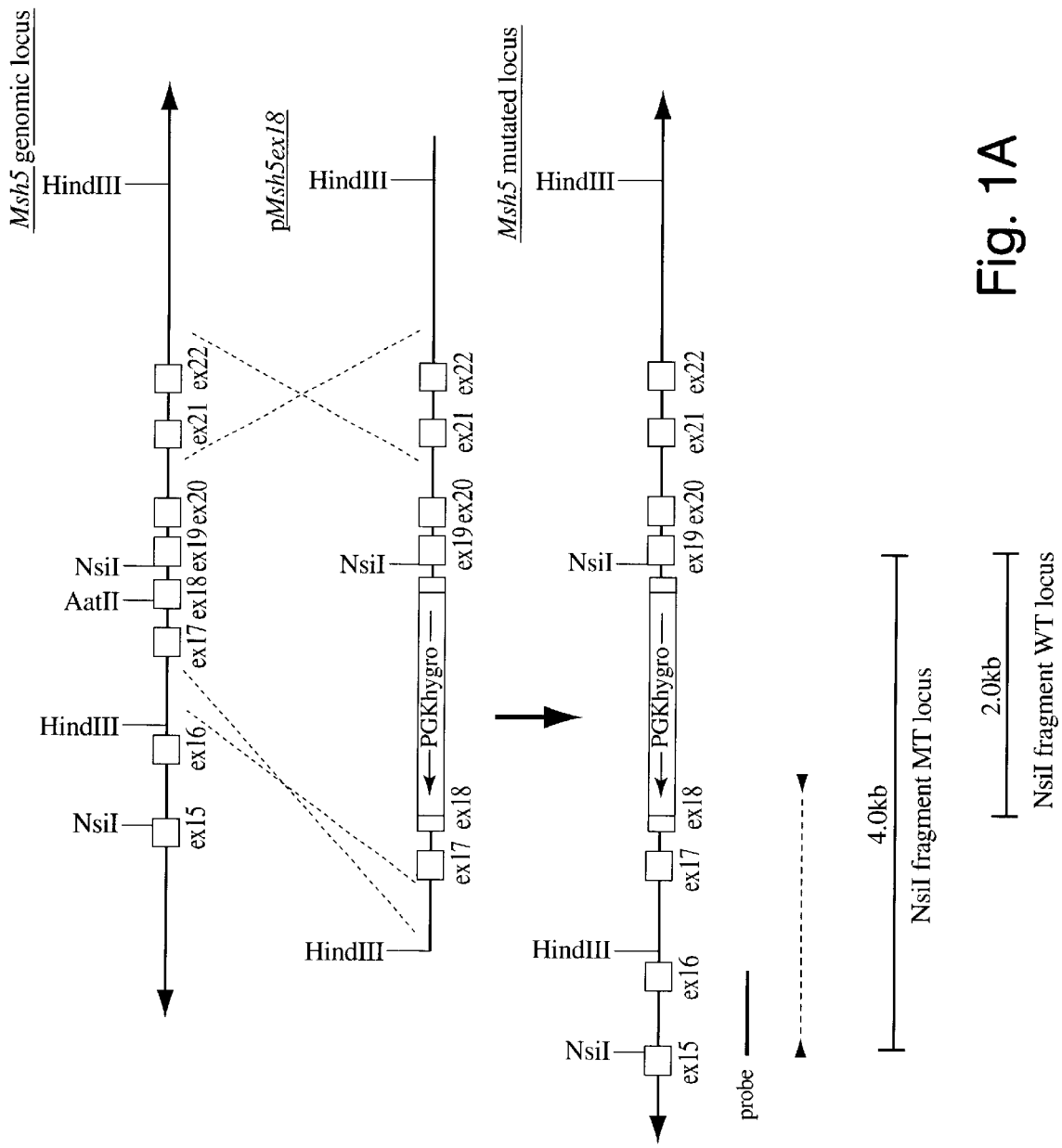
FIGS. 1A–D are a schematic of the generation of Msh5 null mice.

The present invention is based, at least in part, on the generation of animals which are homozygous for a null mutation in the MutS homolog 5 (MSH5) gene and the observation that these animals are sterile. Accordingly, the invention features, a non-human animal, in which the gene encoding the MutS homolog 5 (MSH5) protein is misexpressed. In preferred embodiments the animal, is preferably a transgenic animal.

As used herein, a "transgenic animal" includes an animal, e.g., a non-human mammal, e.g., a swine, a monkey, a goat, or a rodent, e.g., a mouse, in which one or more, and preferably essentially all, of the cells of the animal include a transgene. The transgene is introduced into the cell, directly or indirectly by introduction into a precursor of the cell, e.g., by microinjection, transfection or infection, e.g., by infection with a recombinant virus. The term genetic manipulation includes the introduction of a recombinant DNA molecule. This molecule may be integrated within a chromosome, or it may be extrachromosomally replicating DNA.

As used herein, the term "rodent" refers to all members of the phylogenetic order Rodentia.

As used herein, the term "misexpression" includes a non-wild type pattern of gene expression. Expression as used herein includes transcriptional, post transcriptional, e.g., mRNA stability, translational, and post translational stages. Misexpression includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus. Misexpression includes any expression from a transgenic nucleic acid. Misexpression includes the lack or non-expression of a gene or transgene, e.g., that can be induced by a deletion of all or part of the gene or its control sequences.

As used herein, the term "knockout" refers to an animal or cell therefrom, in which the insertion of a transgene disrupts an endogenous gene in the animal or cell therefrom. This disruption can essentially eliminate MSH5 in the animal or cell.

In preferred embodiments, misexpression of the gene encoding the MSH5 protein is caused by disruption of the MSH5 gene. For example, the MSH5 gene can be disrupted through removal of DNA encoding all or part of the protein.

In preferred embodiments, the animal can be heterozygous or homozygous for a misexpressed MSH5 gene, e.g., it can be a transgenic animal heterozygous or homozygous for an MSH5 transgene.

In preferred embodiments, the animal is a transgenic mouse with a transgenic disruption of the MSH5 gene, preferably an insertion or deletion, which inactivates the gene product.

In another aspect, the invention features, a nucleic acid molecule which, when introduced into an animal or cell, results in the misexpression of the MSH5 gene in the animal or cell. In preferred embodiments, the nucleic acid molecule, includes an MSH5 nucleotide sequence which includes a disruption, e.g., an insertion or deletion and preferably the insertion of a marker sequence. The nucleotide sequence of the wild type MSH5 is known in the art and described in, for example, Winand, N. J. et al. (1998) *Genomics* 53, 69–80, the contents of which are incorporated herein by reference. For example, the nucleic acid molecule can be the targeting construct, shown in FIG. 1.

As used herein, the term "marker sequence" refers to a nucleic acid molecule that (a) is used as part of a nucleic acid construct (e.g., the targeting construct) to disrupt the expression of the gene of interest (e.g., the MSH5 gene) and (b) is used to identify those cells that have incorporated the targeting construct into their genome. For example, the marker sequence can be a sequence encoding a protein which confers a detectable trait on the cell, such as an antibiotic resistance gene, e.g., neomycin resistance gene, or an assayable enzyme not typically found in the cell, e.g., alkaline phosphatase, horseradish peroxidase, luciferase, beta-galactosidase and the like.

As used herein, "disruption of a gene" refers to a change in the gene sequence, e.g., a change in the coding region. Disruption includes: insertions, deletions, point mutations, and rearrangements, e.g., inversions. The disruption can occur in a region of the native MSH5 DNA sequence (e.g., one or more exons) and/or the promoter region of the gene so as to decrease or prevent expression of the gene in a cell as compared to the wild-type or naturally occurring sequence of the gene. The "disruption" can be induced by classical random mutation or by site directed methods. Disruptions can be transgenically introduced. The deletion of an entire gene is a disruption. Preferred disruptions reduce MSH5 levels to about 50% of wild type, in heterozygotes or essentially eliminate MSH5 in homozygotes.

In another aspect, the invention features, a method of evaluating a fertility treatment. The method includes: administering the treatment to an MSH5 misexpressing animal or a cell therefrom; and determining the effect of the treatment on a fertility indication, to thereby evaluate the treatment for fertility. The method may be performed in vivo or in vitro. As used herein, the term "fertility indication" includes any parameter related to fertility, e.g., sperm count, testicular size, or oocyte morphology.

As used herein, "administering a treatment to an animal or cell" is intended to refer to dispensing, delivering or applying a treatment to an animal or cell. In terms of the therapeutic agent, the term "administering" is intended to refer to contacting or dispensing, delivering or applying the therapeutic agent to an animal by any suitable route for delivery of the therapeutic agent to the desired location in the animal, including delivery by either the parenteral or oral route, intramuscular injection, subcutaneous/intradermal injection, intravenous injection, buccal administration, transdermal delivery and administration by the intranasal or respiratory tract route.

In preferred embodiments, the animal or cell is an animal or cell described herein. In other preferred embodiments, the method uses a transgenic mouse in which the expression of the MSH5 gene is inhibited. In yet other preferred embodiments, the method uses a cell derived from a transgenic mouse in which the expression of the MSH5 gene is inhibited.

In another aspect, the invention features, a method for identifying a compound which modulates the activity of MSH5. The method includes contacting MSH5 with a test compound and determining the effect of the test compound on the activity of MSH5 to, thereby, identify a compound which modulates MSH5 activity. In preferred embodiments, the activity of MSH5 is inhibited.

As used herein, the term "compound" includes any agent, e.g., peptides, peptidomimetics, small molecules, or other drugs, which bind to MSH5 proteins, have a stimulatory or inhibitory effect on, for example, MSH5 expression or MSH5 activity, or have a stimulatory or inhibitory effect on, for example, the expression or activity of a MSH5 substrate.

In another aspect, the invention features, a method for modulating the activity of MSH5. The method includes contacting MSH5 or a cell expressing MSH5 with a compound which binds to MSH5 in an amount sufficient to modulate the activity of MSH5. In preferred embodiments, the activity of MSH5 is inhibited, e.g., in contraception.

As used herein, the term "contraception" includes the prevention of fertilization, preferably without destroying fertility.

In another aspect, the invention features, a method of identifying a subject having or at risk of developing a fertility disease or disorder. The method includes obtaining a sample from said subject; contacting the sample with a nucleic acid probe or primer which selectively hybridizes to MSH5 and determining whether aberrant MSH5 expression or activity exists in the sample, thereby, identifying a subject having or at risk of developing a fertility disease or disorder.

As used herein, the term "fertility disease or disorder" includes any disease disorder or condition which affects fertilization. Fertility diseases include conditions in which the development of the gametes, i.e., the ovum and the sperm, is abnormal, as well as conditions in which a fetus cannot be carried to term. Examples of such fertility disorders include low sperm count, habitual abortion, and abnormal ovulation.

In another aspect, the invention features, an isolated cell, or a purified preparation of cells, from an MSH5 misexpressing animal, e.g., an MSH5 misexpressing animal described herein. In preferred embodiments, the cell is a transgenic cell, in which the gene encoding the MSH5 protein is misexpressed. The cell, preferably a transgenic cell is an oocyte or a spermatocyte.

In preferred embodiments, the cell is heterozygous or homozygous for the transgenic mutant gene.

As used herein, the term "transgenic cell" refers to a cell containing a transgene.

As used herein, "purified preparation" is a preparation which includes at least 10%, more preferably 50%, yet more preferably 90% by number or weight of the subject cells.

The present invention is described in further detail in the following subsections.

Preparation of MSH5 Targeting Constructs

The MSH5 nucleotide sequence to be used in producing the targeting construct is digested with a particular restriction enzyme selected to digest at a location(s) such that a new DNA sequence encoding a marker gene can be inserted in the proper position within this MSH5 nucleotide sequence. The marker gene should be inserted such that it can serve to prevent expression of the native gene. The position will depend on various factors such as the restriction sites in the sequence to be cut, and whether an exon sequence or a promoter sequence, or both is (are) to be interrupted (i.e., the precise location of insertion necessary to inhibit MSH5 gene expression). In some cases, it will be desirable to actually remove a portion or even all of one or more exons of the gene to be suppressed so as to keep the length of the targeting construct comparable to the original genomic sequence when the marker gene is inserted in the targeting construct. In these cases, the genomic DNA is cut with appropriate restriction endonucleases such that a fragment of the proper size can be removed.

The marker sequence can be any nucleotide sequence that is detectable and/or assayable. For example, the marker gene can be an antibiotic resistance gene or other gene whose expression in the genome can easily be detected. The marker gene can be linked to its own promoter or to another strong promoter from any source that will be active in the cell into which it is inserted; or it can be transcribed using the promoter of the MSH5 gene. The marker gene can also have a polyA sequence attached to the 3' end of the gene; this sequence serves to terminate transcription of the gene. For example, the marker sequence can be a protein that (a) confers resistance to antibiotics or other toxins; e.g., ampicillin, tetracycline, or kanamycin for prokaryotic host cells, and neomycin, hygromycin, or methotrexate for mammalian cells; (b) complements auxotrophic deficiencies of the cell; or (c) supplies critical nutrients not available from complex media.

After the MSH5 DNA sequence has been digested with the appropriate restriction enzymes, the marker gene sequence is ligated into the MSH5 DNA sequence using methods known to the skilled artisan and described in Sambrook et al., *Molecular Cloning A Laboratory Manual*, 2nd Ed., ed., Cold Spring Harbor Laboratory Press: 1989, the contents of which are incorporated herein by reference.

Preferably, the ends of the DNA fragments to be ligated are compatible; this is accomplished by either restricting all fragments with enzymes that generate compatible ends, or by blunting the ends prior to ligation. Blunting is performed using methods known in the art, such as for example by the use of Klenow fragment (DNA polymerase I) to fill in sticky ends.

The ligated targeting construct can be inserted directly into embryonic stem cells, or it may first be placed into a suitable vector for amplification prior to insertion. Preferred vectors are those that are rapidly amplified in bacterial cells such as the pBluescript II SK vector (Stratagene, San Diego, Calif.) or pGEM7 (Promega Corp., Madison, Wis.).

Construction of Transgenic Mice

Transfection of Embryonic Stem Cells

Mouse embryonic stem cells (ES cells) can be used to generate the transgenic (e.g., knockout) MSH5 mice. Any ES cell line that is capable of integrating into and becoming part of the germ line of a developing embryo, so as to create germ line transmission of the targeting construct is suitable for use herein. For example, a mouse strain that can be used for production of ES cells, is the 129J strain. A preferred ES cell line is murine cell line D3 (American Type Culture Collection catalog no. CRL 1934). The cells can be cultured and prepared for DNA insertion using methods known in the art and described in Robertson, *Teratocarcinomas and Embryonic Stem Cells: A Practical Approach*, E. J. Robertson, ed. IRL Press, Washington, D.C., 1987, in Bradley et al., *Current Topics in Devel Biol.*, 20:357–371, 1986 and in Hogan et al., *Manipulating the Mouse Embryo: A Laboratory Manual*, Cold Spring Harbor Laboratory Press, Cold Spring Harbor, N.Y., 1986, the contents of which are incorporated herein by reference.

The knockout construct can be introduced into the ES cells by methods known in the art, e.g., those described in Sambrook et al. Suitable methods include, electroporation, microinjection, and calcium phosphate treatment methods.

The targeting construct to be introduced into the ES cell is preferably linear. Linearization can be accomplished by digesting the DNA with a suitable restriction endonuclease selected to cut only within the vector sequence and not within the MSH5 gene sequence.

After the introduction of the targeting construct, the cells are screened for the presence of the construct. The cells can be screened using a variety of methods. Where the marker gene is an antibiotic resistance gene, the cells can be cultured in the presence of an otherwise lethal concentration of antibiotic. Those cells that survive have presumably integrated the knockout construct. A southern blot of the ES cell genomic DNA can also be used. If the marker gene is a gene that encodes an enzyme whose activity can be detected (e.g., beta-galactosidase), the enzyme substrate can be added to the cells under suitable conditions, and the enzymatic activity can be analyzed.

To identify those cells with proper integration of the targeting construct, the DNA can be extracted from the ES cells using standard methods. The DNA can then be probed on a southern blot with a probe or probes designed to hybridize in a specific pattern to genomic DNA digested with particular restriction enzymes. Alternatively, or additionally, the genomic DNA can be amplified by PCR with probes specifically designed to amplify DNA fragments of a particular size and sequence such that, only those cells containing the targeting construct in the proper position will generate DNA fragments of the proper size.

Injection/Implantation of Embryos

Procedures for embryo manipulation and microinjection are described in, for example, *Manipulating the Mouse Embryo* (Cold Spring Harbor Laboratory Press, Cold Spring Harbor, N.Y., 1986, the contents of which are incorporated herein by reference). Similar methods are used for production of other transgenic animals. In an exemplary embodiment, mouse zygotes are collected from six week old females that have been super ovulated with pregnant mares serum (PMS) followed 48 hours later with human chorionic gonadotropin. Primed females are placed with males and checked for vaginal plugs on the following morning. Pseudo pregnant females are selected for estrus, placed with proved sterile vasectomized males and used as recipients. Zygotes are collected and cumulus cells removed. Furthermore, blastocytes can be harvested. Pronuclear embryos are recovered from female mice mated to males. Females are treated with pregnant mare serum, PMS, to induce follicular growth and human chorionic gonadotropin, hCG, to induce ovulation. Embryos are recovered in a Dulbecco's modified phosphate buffered saline (DPBS) and maintained in Dulbecco's modified essential medium (DMEM) supplemented with 10% fetal bovine serum.

Microinjection of an MSH5 targeting construct can be performed using standard micro manipulators attached to a microscope. For instance, embryos are typically held in 100 microliter drops of DPBS under oil while being microinjected. DNA solution is microinjected into the male pronucleus. Successful injection is monitored by swelling of the pronucleus. Recombinant ES cells can be injected into blastocytes, using similar techniques. Immediately after injection embryos are transferred to recipient females, e.g. mature mice mated to vasectomized male mice. In a general protocol, recipient females are anesthetized, paralumbar incisions are made to expose the oviducts, and the embryos are transformed into the ampullary region of the oviducts. The body wall is sutured and the skin closed with wound clips.

Screening for the Presence of the Targeting Construct

Transgenic (e.g., knockout) animals can be identified after birth by standard protocols. DNA from tail tissue can be screened for the presence of the targeting construct using southern blots and/or PCR. Offspring that appear to be mosaics are then crossed to each other if they are believed to carry the targeting construct in their germ line to generate homozygous knockout animals. If it is unclear whether the offspring will have germ line transmission, they can be crossed with a parental or other strain and the offspring screened for heterozygosity. The heterozygotes are identified by southern blots and/or PCR amplification of the DNA.

The heterozygotes can then be crossed with each other to generate homozygous transgenic offspring. Homozygotes may be identified by southern blotting of equivalent amounts of genomic DNA from mice that are the product of this cross, as well as mice that are known heterozygotes and wild type mice. Probes to screen the southern blots can be designed as set forth above.

Other means of identifying and characterizing the knockout offspring are known in the art. For example, northern blots can be used to probe the mRNA for the presence or absence of transcripts encoding either the gene knocked out, the marker gene, or both. In addition, western blots can be used to assess the level of expression of the gene knocked out in various tissues of these offspring by probing the western blot with an antibody against the protein encoded by the gene knocked out (e.g., the MSH5 protein), or an antibody against the marker gene product, where this gene is expressed. Finally, in situ analysis (such as fixing the cells and labeling with antibody) and/or FACS (fluorescence activated cell sorting) analysis of various cells from the offspring can be performed using suitable antibodies to look for the presence or absence of the targeting construct gene product.

Other Transgenic Animals

The transgenic animal used in the methods of the invention can be a mammal; a bird; a reptile or an amphibian. Suitable mammals for uses described herein include: ruminants; ungulates; domesticated mammals; and dairy animals. Preferred animals include: goats, sheep, camels, cows, pigs, horses, oxen, llamas, chickens, geese, and turkeys. Methods for the preparation and use of such animals are known in the art. A protocol for the production of a transgenic pig can be found in White and Yannoutsos, *Current Topics in Complement Research*: 64th *Forum in Immunology*, pp. 88–94; U.S. Pat. No. 5,523,226; U.S. Pat. No. 5,573,933; PCT Application WO93/25071; and PCT Application WO95/04744. A protocol for the production of a transgenic rat can be found in Bader and Ganten, *Clinical and Experimental Pharmacology and Physiology*, Supp. 3:S81–S87, 1996. A protocol for the production of a transgenic cow can be found in *Transgenic Animal Technology, A Handbook*, 1994, ed., Carl A. Pinkert, Academic Press, Inc. A protocol for the production of a transgenic sheep can be found in *Transgenic Animal Technology, A Handbook*, 1994, ed., Carl A. Pinkert, Academic Press, Inc.

Uses of MSH5 Transgenic Mice

MSH5 misexpressing animals, e.g., mice, or cells can be used to screen treatments for MSH5-related disorders, e.g., fertility disorders. The candidate treatment can be administered over a range of doses to the animal or cell. Efficacy can be assayed at various time points for the effects of the treatment on the disorder being evaluated.

Such treatments can be evaluated by determining the effect of the treatment on a fertility indication. Such parameters include sperm count, testicular size, or oocyte morphology. For example, treatment of a fertility condition includes treatment of ovary degeneration in the animal to, thereby, identify treatments suitable for administration to human subjects.

Methods of the invention can be used to study cells derived from the MSH5 ablated animals in order to define the mechanism of MSH5 function in cell processes, e.g., meiosis. For example, cells can be isolated from MSH5 misexpressing animals and used to identify agents that act downstream from MSH5 in the MSH5 pathway or in independent pathways.

Candidate Treatments

The candidate treatment, which is evaluated using methods described herein, can include: (a) the administration of a therapeutic agent (e.g., a drug, a chemical, an antibody, a protein, a nucleic acid or other substance) to a MSH5 misexpressing animal or cell; (b) the administration of a diet regimen to an MSH5 misexpressing animal; (c) the administration of ionizing radiation to an MSH5 misexpressing animal or cell. Any combination of the afore-mentioned treatments can be administered to an MSH5 misexpressing animal or cell. The treatment can be administered prior to, simultaneously and/or after the onset of the disorder or condition, for which the candidate treatment is being evaluated. The therapeutic agent can be administered to a MSH5 misexpressing animal, orally, parenterally or topically.

Predictive/Diagnostic Assays

The present invention also pertains to the field of predictive medicine in which diagnostic and prognostic assays are used for prognostic (predictive) purposes to thereby treat an individual prophylactically. Accordingly, one aspect of the present invention relates to diagnostic assays for determining MSH5 protein and/or nucleic acid expression as well as MSH5 activity, in the context of a biological sample (e.g., blood, serum, cells, tissue) to thereby determine whether an individual is afflicted with a disease or disorder, or is at risk of developing a disorder, associated with aberrant MSH5 expression or activity, e.g., infertility. The invention also provides for prognostic (or predictive) assays for determining whether an individual is at risk of developing a disorder associated with MSH5 protein, nucleic acid expression or activity. For example, mutations in an MSH5 gene can be assayed in a biological sample. Such assays can be used for prognostic or predictive purpose to thereby phophylactically treat an individual prior to the onset of a disorder characterized by or associated with MSH5 protein, nucleic acid expression or activity.

Screening Assays

The invention provides a method (also referred to herein as a "screening assay") for identifying modulators, i.e., candidate or test compounds or agents (e.g., peptides, peptidomimetics, small molecules or other drugs) which bind to MSH5 proteins, have a stimulatory or inhibitory effect on, for example, MSH5 expression or MSH5 activity, or have a stimulatory or inhibitory effect on, for example, the expression or activity of an MSH5 substrate.

In one embodiment, the invention provides assays for screening candidate or test compounds which are substrates of an MSH5 protein or polypeptide or biologically active portion thereof. In another embodiment, the invention provides assays for screening candidate or test compounds which bind to or modulate the activity of an MSH5 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Therapeutic Methods

Another aspect of the invention pertains to methods of modulating MSH5 expression or activity for therapeutic purposes. Accordingly, in an exemplary embodiment, the modulatory method of the invention involves contacting a cell with MSH5 or an agent that modulates one or more of the activities of the MSH5 protein. An agent that modulates MSH5 protein activity can be a nucleic acid or a protein, a naturally-occurring target molecule of an MSH5 protein an MSH5 antibody, an MSH5 agonist or antagonist, a peptidomimetic of an MSH5 agonist or antagonist, or other small molecule. In one embodiment, the agent stimulates one or more MSH5 activities. Examples of such stimulatory agents include active MSH5 protein and a nucleic acid molecule encoding MSH5 that has been introduced into the cell. In another embodiment, the agent inhibits one or more MSH5 activites. Examples of such inhibitory agents include antisense MSH5 nucleic acid molecules, anti-MSH5 antibodies, and MSH5 inhibitors. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a MSH5 protein or nucleic acid molecule, e.g., a fertility disorder. In one embodiment, the method involves administering an agent (e.g., an agent identified by a screening assay described herein), or combination of agents that modulates (e.g., upregulates or downregulates) MSH5 expression or activity. In another embodiment, the method involves administering an MSH5 protein or nucleic acid molecule as therapy to compensate for reduced or aberrant MSH5 expression or activity.

Stimulation of MSH5 activity is desirable in situations in which MSH5 is abnormally downregulated and/or in which increased MSH5 activity is likely to have a beneficial effect. For example, stimulation of MSH5 activity is desirable in situations in which a MSH5 is downregulated and/or in which increased MSH5 activity is likely to have a beneficial effect. Likewise, inhibition of MSH5 activity is desirable in situations in which MSH5 is abnormally upregulated and/or in which decreased MSH5 activity is likely to have a beneficial effect.

This invention is farther illustrated by the following examples which should not be construed as limiting. The contents of all references, patents and published patent applications cited throughout this application are incorporated herein by reference.

EXAMPLES

Materials and Methods

Mouse Msh5 cDNA Cloning

The original segment of the mouse Msh5 gene was obtained by PCR using BALB/c genomic DNA (Clontech) and primers GTGCTGTGGAATTCAGGATAC (sense; SEQ ID NO: 1) and CCAGAACTCTCTGGAGAAGC (antisense; SEQ ID NO:2) based on the human cDNA sequence. The remainder of the mouse Msh5 coding sequence was cloned by RT-PCR using the Advantage cDNA PCR Kit and gene-specific primers CTCCACTATC-CACTTCATGCCAGATGC (sense; SEQ ID NO:3) and GCTGGGGAGGACACTGGAAGGACTCTCA (antisense, based on human 3'-untranslated cDNA sequence; SEQ ID NO:4).

The mouse Msh5 genomic locus was cloned from a P1 mouse embryonic stem cell genomic library screened by Genome Systems, Inc. which yielded three clones 30 11051, 11052, and 11053.

Construction of the pMsh5ex18 Targeting Vectors

A genomic Msh5 fragment containing exon 18 was obtained by screening a mouse genomic Charon 35, 129/Ola phage library. A 3.8 kb HindIII fragment containing exon 18 was subcloned into pBluescript SK+/− and a 2.0 kb BglII PGKhygro cassette was cloned into the AatII site at codon 528 in exon 18 using BglII/AatII adaptors. The resulting gene targeting clone was designated pMsh5ex18.

Electroporation of Embryonic Stem Cells

The targeting vector pMsh5ex18 (50 ug) was electroporated into WW6 ES cells (described in Ioffe, E. et al. (1995) *Proc. Natl. Acad. Sci. USA* 92, 7357–7361) and hygromycin resistant colonies were isolated and screened by PCR using forward primer A 5'-AGCTGGAGAACCTGGACTCTC-3' (SEQ ID NO:5) and reverse primer B 5'-TGGAAGGATTGGAGCTACGG-3' (SEQ ID NO:6). Positive ES cell colonies were identified by a 1.5 kb PCR fragment specific for the targeting event. Six positive cell lines MSH5-1, MSH5-33, MSH5-41, MSH5-52, MSH5-58, and MSH5-109 were identified and the correct targeting event was shown by NsiI digestion of high molecular weight DNA and Southern Blot analysis using a 0.8 kb EcoRI/HindIII probe directed at the 5' intron region between exons 13 and 14 that is not included in the targeting vector.

Northern Blot Analysis

Four $\mu$g of polyA RNA from 24 day old males was separated on 1.0% Agarose Formaldehyde gels, transferred onto Nitrocellulose membrane and hybridized with an Msh5 probe corresponding to exons 3 to 8, a probe spanning the complete mouse Msh4 cDNA and a human β-actin probe.

Western Blot Analysis

For Western blot analysis equal amounts of protein from testes extracts of 23 day old males were separated on a 10% SDS-polyacrylamide gel and transferred onto a Immobilon-P (Millipore) membrane. The membrane was blocked in TBS, 0.1% Tween-20,5% nonfat dry milk, 10% goat serum (Sigma) and incubated with 1:1,000 diluted primary anti-MSH5 antibody. Bound protein was detected by chemiluminescence using a 1:30,000 diluted goat anti-mouse IgG horseradish peroxidase conjugate (Sigma).

Histology

Ovaries from Msh5$^{+/+}$ and Msh5$^{−/−}$ females between e 18 and 5 wks postpartum (pp) were removed and fixed in Bouins or 4% buffered formalin for 30–360 minutes before transferring to 70% ethanol. Testes were fixed by transcardiac perfusion of 4% buffered formalin and then overnight in fresh fixative. All tissues were processed for histology by routine methods and were sectioned at 3 or 5 μm.

Chromosomes

Chromosome spreads were prepared according to the method of Counce and Meyer (described in Counce, S. J. & Meyer, G. F. (1973) *Chromosoma* 44, 231–253, the contents of which are incorporated herin by reference), with modifications. Spreads were then either silver stained in 50% silver nitrate at 65° C. for 6 hours (for electron microscopy) or subjected to immunofluorescence localization of chromosomally-associated proteins, according to the method of Moens (described in Spyropoulos, B. & Moens, P. B. (1994) *Methods in Molecular Biology* 33, 131–139, the contents of which are incorporated herein by reference).

Example 1

Generation and Analysis of Msh5$^{-/-}$ Mice

To assess the role of MSH5 in mammals, mice with a null mutation in Msh5 were generated and characterized. Msh5$^{-/-}$ mice are viable but are sterile. Meiosis in these mice is severely affected owing to the disruption of chromosome pairing in prophase I. This meiotic failure leads to a diminution in testicular size and a complete loss of ovarian structures. These results show that normal MSH5 function is essential for meiotic progression and, in females, gonadal maintenance.

Figure 1B:
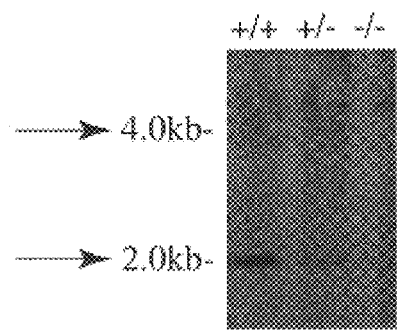
Figure 1C:
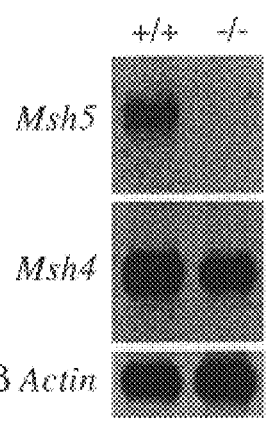
Figure 1D:
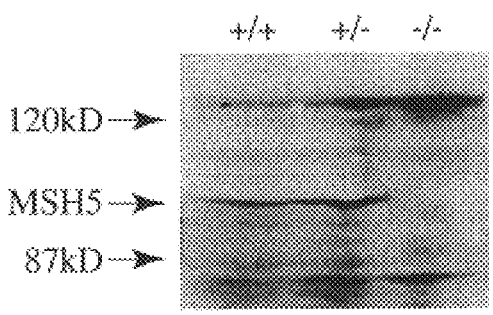
Figure 2A:
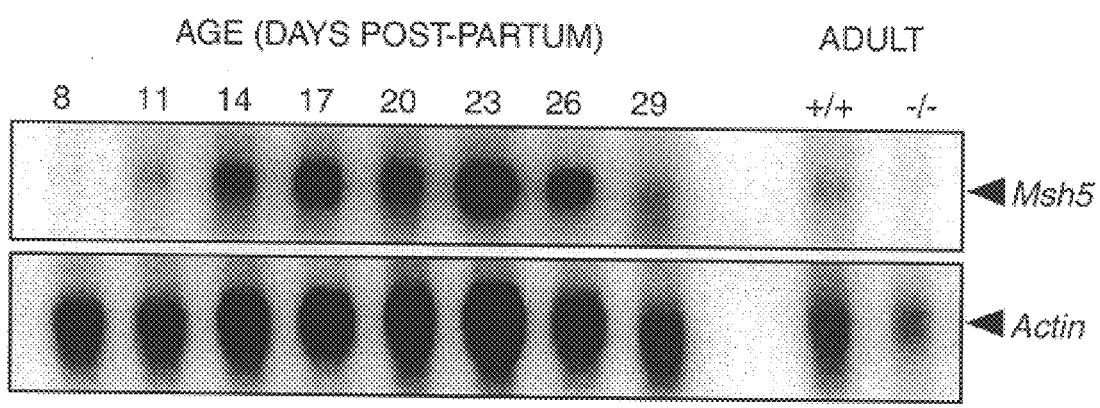
FIGS. 2A–G depicts the disruption of spermatogenesis in Msh5$^{-/-}$ males.
Figure 2B:
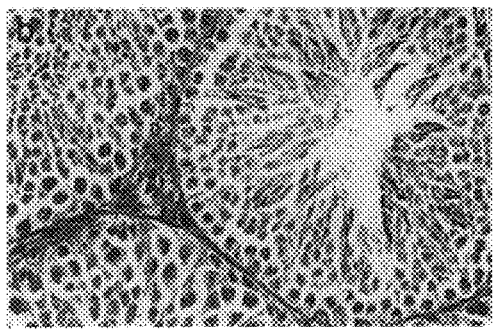
Figure 2C:
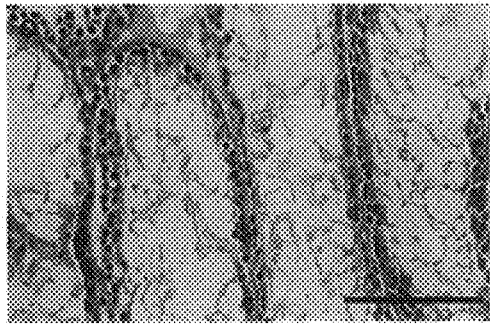
Figure 2D:
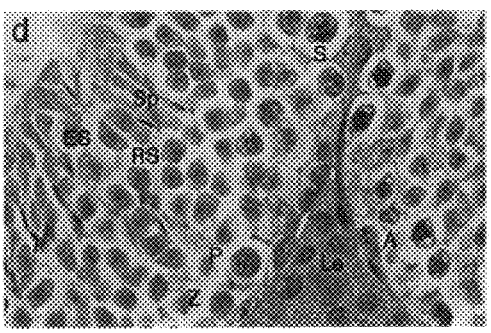
Figure 2E:
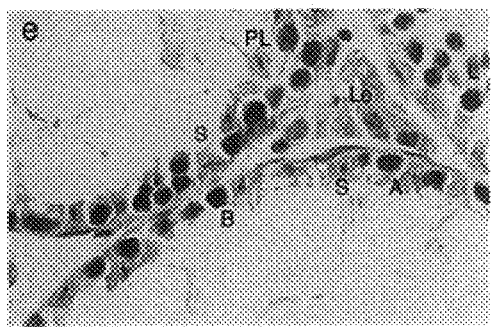
Figure 2F:
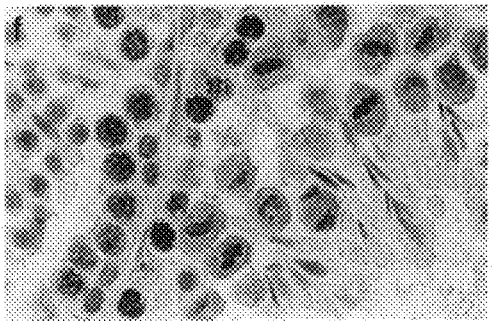
Figure 2G:
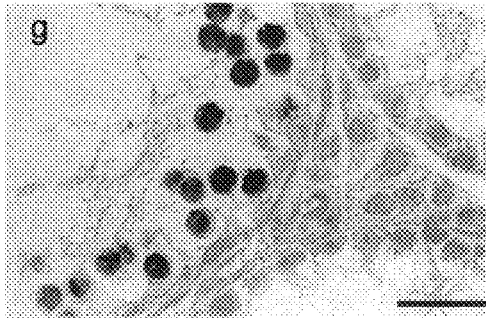
Figure 4A:
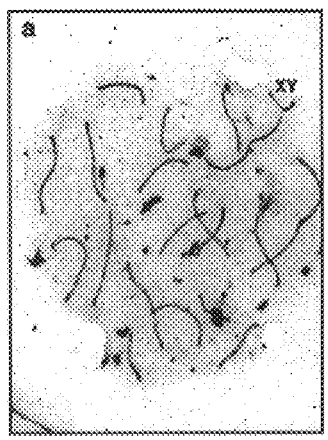
FIGS. 4A–C depicts the disruption of meiosis prior to synapsis in Msh5 spermatocytes.
Figure 4B:
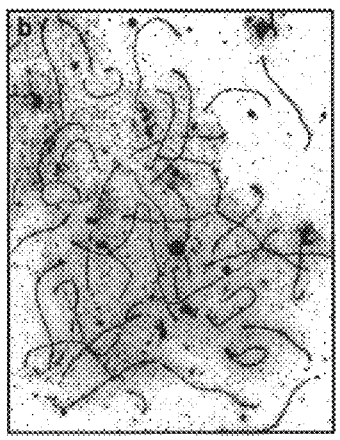
Figure 4C:
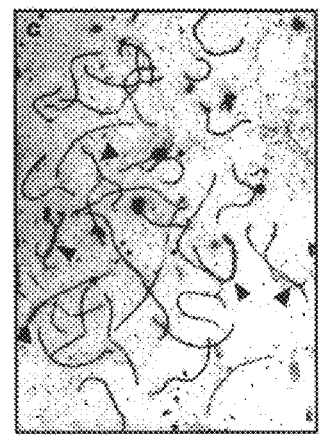

A mouse Msh5 genomic clone was isolated and used to construct a gene targeting vector (see FIG. 1A) that was used to generate mice from two ES cell lines with the modified MshS locus (see FIG. 1B). The mice transmitted the modified locus in a Mendelian fashion and homozygous Msh5$^{-/-}$ mice were viable. Msh5 transcripts or protein were not detectable in testes of 24 day old mice (see FIG. 1D). These data indicate that the modified Msh5 locus does not encode a functional MSH5 protein. prophase I commencing at day 13. Msh5 is highly expressed in the gonads of humans and mice, and in the latter is co-incident with the onset of the meiotic wave. Msh5$^{-/-}$ males exhibited normal sexual behavior, but they were infertile due to the complete absence of epididymal spermatozoa. Examination of seminiferous tubules in Msh5$^{-/-}$ adult males revealed a severe disruption of spermatogenesis (see FIG. 2B, C), causing a 70% reduction in testis size. Interstitial Leydig cells and tubular Sertoli cells are present in the mutant males, as are type A and B spermatogonia, but no normal pachytene spermatocytes are observed (see FIG. 2D–G). At day 17 pp, the seminiferous epithelium of Msh5$^{-/-}$ males, are fairly densely packed, although early signs of germ cell loss are evident, both by reduced germ cell nuclear antigen 1 (GCNA1, described in Enders, G. C. & May, J. J. (1994) *Developmental Biology*. 163, 331–340, the contents of which are incorporated herein by reference) localization and by increased apoptosis (see FIG. 3A, B, C, D). By day 23 pp, the tubules of wild-type mice contain round spermatids (see FIG. 3E, G). In contrast, elevated levels of apoptosis in Msh5$^{-/-}$ tubules leads to continued germ cell attrition (see FIG. 3F, H) and by adulthood, almost the entire spermatogenic cell population is lost. To analyze meiotic progression, meiotic chromosome spreads were examined at the light and electron microscope level. In 23 day old wild-type spreads, silver staining revealed a range of chromosomal configurations, including those at leptotene, zygotene, pachytene and diplotene (see FIG. 4A). However, from four Msh5$^{-/-}$ males it was found that 588/602 (97.7%) spermatocytes contained no synapsed chromosomes (see FIG. 4B) compared to >92% of wild-type cells (255/277) showing chromosomal configurations at zygotene and beyond. All of the spermatocytes from Msh5$^{-/-}$ males contained univalent chromosomes and condensation levels corresponding to zygotene/pachytene stages of meiosis. In the remaining 14 cells only 29 partially paired chromosomes were observed out of the expected 280 pairs (see FIG. 4C). At least half of these (15/29) involved chromosomes of different lengths suggesting that this pairing is non-homologous.

The chromosomal association of SYCP 1, SYCP3 and RAD51 proteins known to be required for recombination and formation of the synaptonemal complex (SC) (Moens, P. B. et al. (1998) *Current Topics in Molecular Biology* 37, 241–263; Plug, A. W., et al. (1996) *Proc. Vatl. Acad Sci. USA* 93, 5920–5924) was also examined. Immunofluorescent localization of SYCP1 and SYCP3 on meiotic chromosomes using a combined antiserum demonstrated normal acquisition of SC in spermatocytes from wild-type males and identified pachytene spermatocytes as having 20 distinct condensed pairs of bivalents. In Msh5$^{-/-}$ spermatocytes, all of the chromosomes were clearly associated with the SYCP1/SYCP3 signal, indicating that axial element formation has been achieved but no condensed bivalents were observed. In Msh5$^{-/-}$ spermatocytes, RAD51 is localized in discrete foci along the univalent chromosomes, and the number and intensity of these foci appears greater in the majority of Msh5$^{-/-}$ cells than on leptotene or zygotene chromosomes from wild-type males and does not decline as observed in wild-type spermatocytes suggesting lack of progress towards pachytene. The presence of RAD51 on unsynapsed chromosomes mutant mice suggests that meiosis is initiated and that double strand breaks might proceed in the absence of MSH5.

Figure 5A:
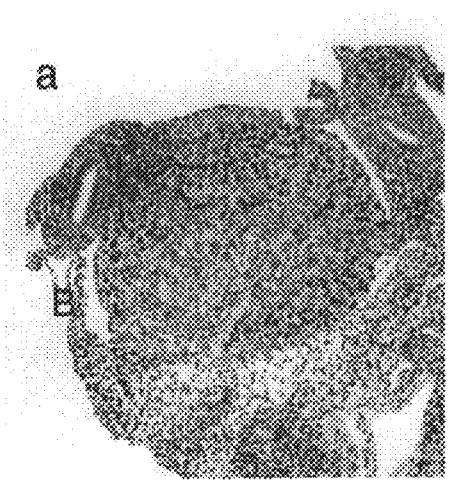
FIGS. 5A–F depicts the loss of oocytes and subsequent ovarian degeneration in Msh5$^{-/-}$ females.
Figure 5B:
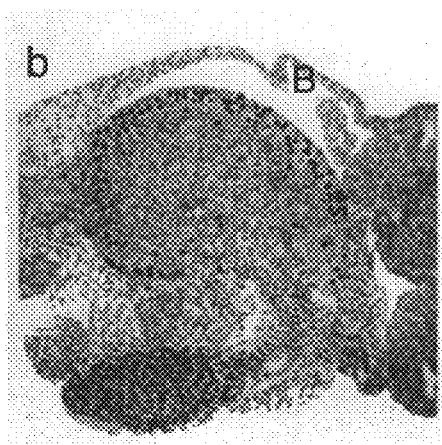
Figure 5C:
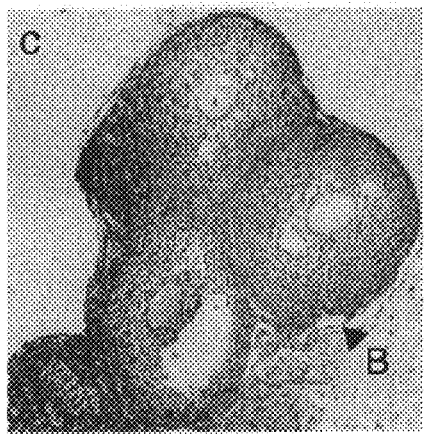
Figure 5D:
Figure 5E:
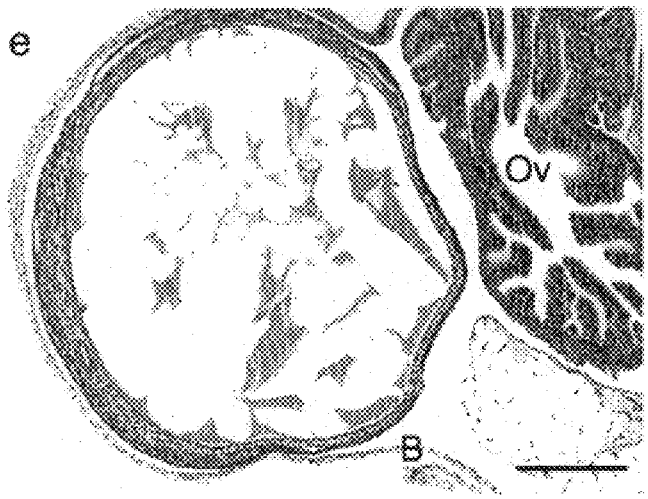
Figure 5F:
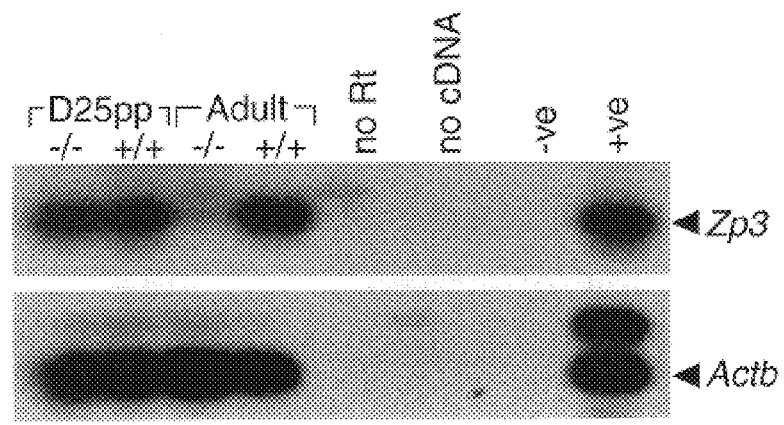

To examine the role of MSH5 in female meiosis, ovarian function was assessed in Msh5$^{-/-}$ adults. The mutants did not mate with wild-type males, nor did they undergo normal estrous cycles. The Msh5$^{-/-}$ females have normally structured oviducts and uteri but lack discernible ovaries (see FIG. 5D,E). Instead, the ovarian bursa of Msh5 females was empty or, more frequently, contained cystic structures with 1–4 cysts (see FIG. 5E). At day 3 pp, the ovaries of Msh5$^{-/-}$ females contained fewer oocytes (see FIG. 5A,B). By day 25 pp, the ovaries of Msh5$^{-/-}$ females were reduced to a small grouping of 1–3 follicles that appeared to be at post-antral stages of development, and occasionally contained oocytes (see FIG. 5C) while wild-type ovaries have abundant primordial follicles. The presence of oocytes in day 25 pp Msh5$^{-/-}$ females was confirmed by RT-PCR detection of transcripts for the oocyte-specific protein, zona pellucida 3 (ZP3) described in Wassarman, P. M. (1998) *Annual Review of Biochemistry*. 57, 415–442, the contents of which are incorporated herein by reference. However, in adults ZP3 transcripts could only be detected in wild-type ovaries (see FIG. 5F). Thus, the ovaries of Msh5$^{-/-}$ females are normal size at birth, but degenerate progressively to become rudimentary, concomitant with the decline in oocyte numbers from before day 3 pp until adulthood.

Figure 6A:
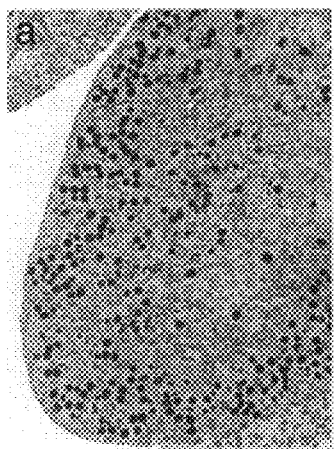
FIGS. 6A–J shows that the disruption of oogenesis in Msh5$^{-/-}$ females leads to a failure of folliculogenesis.
Figure 6B:
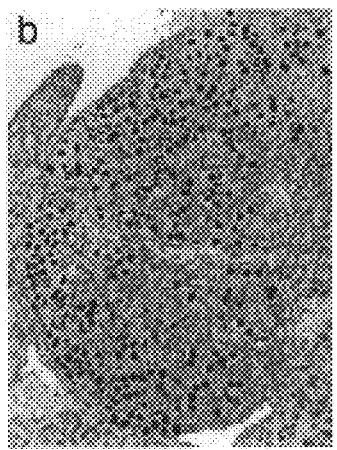
Figure 6C:
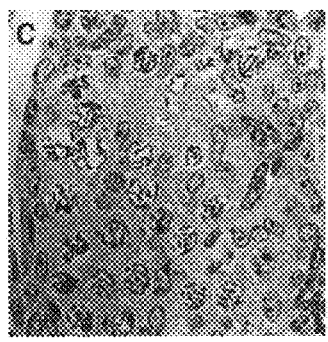
Figure 6E:
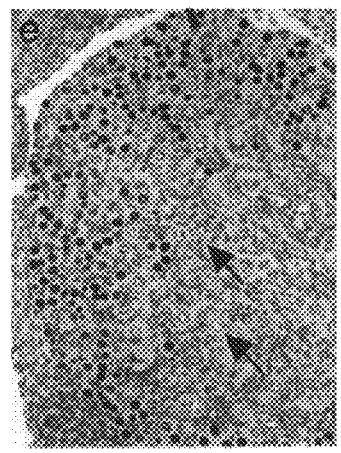
Figure 6F:
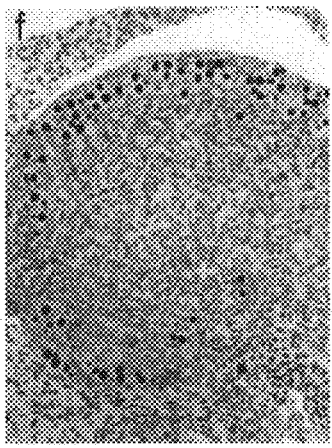
Figure 6D:
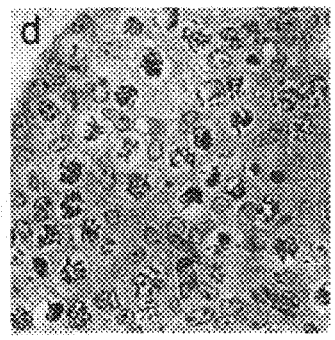
Figure 6G:
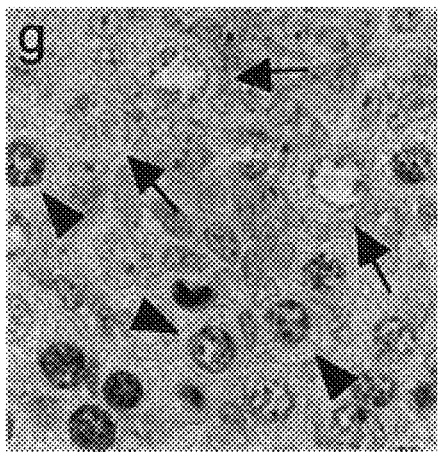
Figure 6H:
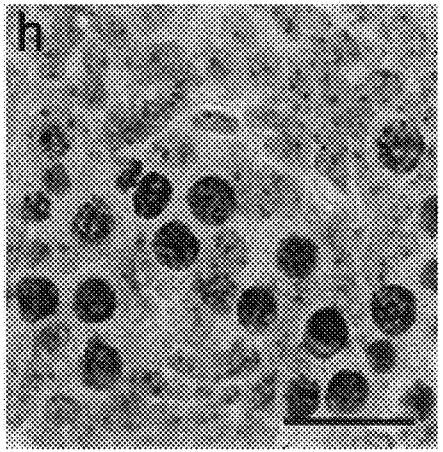
Figure 6I:
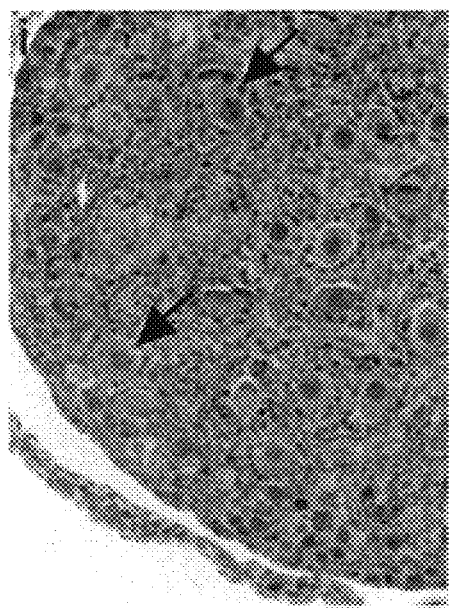
Figure 6J:

Msh5 expression was examined in wild-type ovaries by RT-PCR. Msh5 expression was detected in e16, e18 and day 1 pp ovaries coincident with the initiation of meiosis in females and consistent with the possibility that MSH5 plays a direct role in ovarian meiosis. During late embryogenesis, the ovaries of homozygous mutant females contain normal numbers of oocytes (see FIG. 6A, C). However, examination of H&E sections revealed subtle differences in chromosome structure between wildtype and Msh5$^{-/-}$ oocytes, characterized by clumping of nuclear contents in the homozygous mutant oocytes (see FIG. 6D) compared to readily identifiable chromosomes in the wild-type oocytes (see FIG. 6B). By day 3 pp, the number of oocytes in the ovaries of Msh5$^{-/-}$ females was dramatically lower than that in wild-type ovaries (see FIG. 6E,G) and did not exhibit the GCNA1 staining characteristic of pachytene oocytes (see FIG. 6F,H). By day 6 pp, large, primordial follicles containing readily identifiable oocytes were distributed throughout the ovary of wild-type females (see FIG. 6I, J), while in ovaries from Msh5$^{-/-}$ females the oocyte pool was severely diminished.

The results show that MSH5 is required for chromosome pairing and/or synapsis. Mutations in the other mouse MutHLS genes, Pms2 and Mlh1, which interact with MSH homologs, are also sterile due to meiotic abnormalities. However, the stage at which meiosis is aberrant in these mice is different. In Pms2$^{-/-}$ mice, chromosome pairing is disrupted but spermatids and spermatozoa, although abnormal, were observed. In Mlh1$^{-/-}$ mice, normal pairing was detected but post-pachytene meiotic stages were rarely observed. These results suggest that these proteins have distinct roles at different stages of meiosis.

In adult Msh5$^{-/-}$ females, the phenotype is even more dramatic than in males because of the complete loss of ovarian structures. Similar to the Msh5$^{-/-}$ males, the germ cells populate the genital ridge but the oocytes never progress beyond zygotene. The progressive loss of oocytes from e 18 appears to result from meiotic failure and the activation of a checkpoint resulting in apoptosis, as seen in Msh5$^{-/-}$ spermatocytes. This results in an almost complete absence of oocytes by day 6 pp and the ovary begins to degenerate such that, in the adult, it is usually entirely absent or consists of a few large cysts. The degenerating oocytes fail to initiate folliculogenesis showing that there must be dialog between the oocyte and the surrounding stroma for this process and to maintain ovarian morphology. The phenotype of Msh5$^{-/-}$ females differs from that seen in Dmc1$^{-/-}$ mice which also show a failure of pairing/synapsis and oocyte loss in early neonatal life but retain at least a rudimentary ovary in adulthood. These differences suggest that either the requirement for MSH5 is slightly earlier than DMC 1 or there is partial redundancy for DMC 1 function.

There are similarities in the ovarian phenotype in female Msh5$^{-/-}$ mice and Turner syndrome patients. In both cases there is a rapid loss of oocytes during intrauterine and neonatal life and consequent ovarian degeneration. It is possible that the failure of homologous chromosome pairing, whether at the level of the X chromosome (as in Turner patients) or throughout the entire chromosome population (as in Msh5$^{-/-}$ oocytes) triggers an apoptotic checkpoint that ultimately results in complete ovarian degeneration.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A transgenic mouse whose genome comprises a homozygous null mutation in the endogenous MSH5 gene, wherein said mouse exhibits abnormal development of the gonads.

2. An isolated cell, or a purified preparation of cells from a transgenic mouse whose genome comprises a homozygous null matation in the endogenous MSH5 gene, wherein production of functional MSH5 is inhibited.

3. A method of evaluating a fertility treatment, comprising:
administering said treatment to a transgenic mouse whose genome comprises a null mutation in the endogenous MS5 gene, wherein said mouse exhibits abnormal development of the gonads and is infertile, and determining the effect of the treatment on fertility of said mouse, thereby evaluating said fertility treatment.

4. The method of claim 3, wherein said treatment is evaluated in vivo.

5. The method of claim 3, wherein said treatment is evaluated in vitro.

6. The method of claim 3, wherein the effect of the treatment is determined by sperm count.

7. The method of claim 3, wherein the effect of The treatment is determined by testicular size.

8. The method of claim 3, wherein the effect of the treatment is determined by oocyte morphology.

9. The method of claim 3, wherein the effect of the treatment is determined by sperm morphology.

10. The method of claim 3, wherein the effect of the treatment is determined by gamete morphology.

11. The method of claim 3, wherein the effect of the treatment is determined by chromosome morphology.

12. The method of claim 3, wherein the effect of the treatment is determined by the ability of chromosomes to pair.

13. The method of claim 3, wherein the effect of the treatment is determined by the ability of the mice to mate.

14. The method of claim 3, wherein the effect of the treatment is determined by the ability of the mice to have normal estrous cycles.

15. The method of claim 3, wherein the effect of the treatment is determined by ovarian morphology.

16. A transgenic mouse whose genome comprises a homozygous null mutation in the endogenous MSH5 gene, wherein said mouse is generated by homologous recombination and exhibits abnormal development of the gonads.

* * * * *

UNITED STATES PATENT AND TRADEMARK OFFICE
CERTIFICATE OF CORRECTION

PATENT NO.      : 6,444,873 B1
DATED           : September 3, 2002
INVENTOR(S)     : Edelmann et al.

It is certified that error appears in the above-identified patent and that said Letters Patent is hereby corrected as shown below:

Column 17,
Line 47, replace "MS5" with -- MSH5 --
Line 57, after the word "of" replace the word "The" with the word -- the --

Signed and Sealed this

Eleventh Day of February, 2003

JAMES E. ROGAN
*Director of the United States Patent and Trademark Office*

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 1
gtgctgtgga attcaggata c                                    21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 2
ccagaactct ctggagaagc                                      20

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 3
ctccactatc cacttcatgc cagatgc                              27

```
<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 4
gctggggagg acactggaag gactctca                                              28

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 5
agctggagaa cctggactct c                                                     21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 6
tggaaggatt ggagctacgg                                                       20
```